United States Patent [19]

Giuseppe

[11] Patent Number: 5,393,517
[45] Date of Patent: Feb. 28, 1995

[54] SUNSCREENING COMPOSITIONS CONTAINING 1,3,5-TRIAZINE DERIVATIVES

[75] Inventor: Raspanti Giuseppe, Bergamo, Italy

[73] Assignee: 3V Sigma S.p.A., Milan, Italy

[21] Appl. No.: 57,828

[22] Filed: May 7, 1993

Related U.S. Application Data

[62] Division of Ser. No. 889,963, May 29, 1992, Pat. No. 5,233,040.

[30] Foreign Application Priority Data

Jun. 4, 1991 [IT] Italy .................... MI91A001519

[51] Int. Cl.$^6$ .................. A61K 7/42; A61K 7/44; A61K 7/48

[52] U.S. Cl. ........................... 424/60; 514/245
[58] Field of Search ...................... 424/59, 60

[56] References Cited

U.S. PATENT DOCUMENTS 3,928,373 12/1975 Beck et al. ................... 424/59
3,983,132 9/1976 Strohel ......................... 424/59

*Primary Examiner*—Dale R. Ore
*Attorney, Agent, or Firm*—Griffin Butler Whisenhunt & Kurtossy

[57] ABSTRACT

Derivatives of 2,4,6-tris-[(p-carboxy)-anilino]-5-triazine are described, which can be used as light stabilizers for synthetic polymers and for the preparation of cosmetic and dermatological compositions.

6 Claims, No Drawings

SUNSCREENING COMPOSITIONS CONTAINING 1,3,5-TRIAZINE DERIVATIVES

This is a divisional application of Ser. No. 07/889,963, filed May 29, 1992, U.S. Pat. No. 5,235,040.

The present invention relates to 1,3,5-triazine derivatives of the general formula:

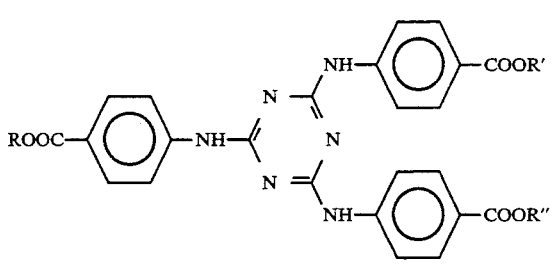

in which
R is $C_5$–$C_{12}$cycloalkyl which may be mono- or poly-substituted by $C_1$–$C_4$alkyl, or a group of the formula (II), (III) or (IV):

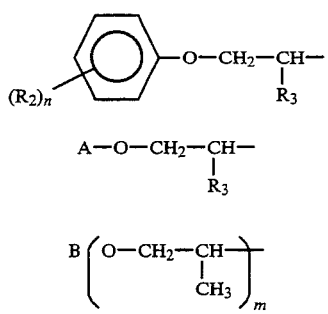

in which $R_2$ is $C_1$–$C_9$alkyl,
n can be an integer from 0 to 3,
$R_3$ is hydrogen or methyl,
A is $C_5$–$C_8$cycloalkyl or $C_4$–$C_8$alkyl,
B is $C_1$–$C_4$alkyl,
m can be an integer from 1 to 10, and
R' and R" which are the same or different, can have the same meaning as R or they are hydrogen, an alkali metal, an ammonium group which may be substituted by alkyl or hydroxyalkyl radicals, or $C_1$–$C_{18}$alkyl,
and to a process for their preparation and to their use as light stabilisers.

As is known, the ultraviolet radiation in sunlight exerts a damaging action on skin tissue and causes degradation of polymers. By means of using particular compounds, so-called sunscreens, which are capable of absorbing the UV part of solar radiation, it is possible to inhibit or at least to slow down its noxious effects and the ageing of skin and of synthetic polymer materials.

Numerous substances have been studied as protective agents and used in experiments, and there is extensive patent literature on this subject, wherein compounds belonging to various chemical classes are proposed, which are capable of absorbing in the ultraviolet region and particularly the most noxious radiation between 290 and 320 nm, so-called here UVB.

Of these compounds, however, only relatively few have proved suitable for application in practice, including esters of p-methoxycinnamic acid and p-dimethylaminobenzoic acid, benzotriazoles and hydroxybenzophenones.

A common disadvantage of all these compounds is their low absorbance, so that it is necessary to use relatively large quantities to obtain the best light-protective capacity, that is to say their so-called sun "protection factor" is relatively low. The sun protection factor (SPF), is a unit of measurement of the light-protective power of a sunscreen or of a cosmetic formulation containing one or more sunscreens. It is directly correlated to the specific extinction and is determined in vivo, by tests on human subjects.

These tests are very time-consuming and expensive, so that various attempts have been made to develop techniques which are suitable for determining the SPF in vitro. One method of determining the SPF in vitro, which has given sufficiently reliable results, is that described by B. L. Diffey and J. Robson in J. Soc. Cosmet. Chem. 40, 127-133 (1989). This method consists in using a synthetic material, Transpore, as a substitute for human skin and in spectroradiometric measurement of the UV radiation from a sunscreen, applied to the above mentioned substrate. The results thus obtained with sunscreens which are known and already used in cosmetics, are very close to those obtained experimentally in vivo.

In the Patent DE 3,206,398, novel sunscreens are described which are derived from s-triazine and are obtained by reacting dichlorotriazine with esters of p-aminobenzoic acid. These compounds absorb very intensively in the UVB zone and consequently show a much higher SPF than previously known sunscreens.

It has now been found that the compounds of the invention have an unexpectedly high SPF, higher than that of the products of DE 3,206,398. A further subject of the invention is therefore the use of the compounds of the formula (I) as sunscreens and light stabilisers.

The compounds of the invention can be usefully employed in the light stabilisation of synthetic polymers, against the solar radiation band between 290 and 320 nm, in order to avoid photodegradation and alterations. It has also been found that the compounds of the formula (I) have a surprising high protective activity on skin against the damaging component of solar radiation.

The compounds according to the present invention can be prepared by reacting symmetrical trichlorotriazine or tribromotriazine with esters of p-aminobenzoic acid of the formula (V)

in which $R_4$ is as defined above for R, R' and R".

Suitable solvents, in which the reaction can be carried out, are those which are inert towards the reagents, for example acetonitrile, ketones such as acetone and methyl ethyl ketone, ethers such as diethyl ether, diisopropyl ether, tetrahydrofuran and dioxane, and aliphatic or aromatic hydrocarbons such as pentane, heptane, cyclohexane, benzene, toluene, xylene or mixtures thereof.

The reaction can be carried out in the absence or presence of acid acceptors, for example hydroxides of alkali metals or alkaline earth metals, or bicarbonates or carbonates of alkali metals, in molar ratios of 3-4 mole of ester of p-aminobenzoic acid per one mole of trichlorotriazine.

If the substituents R, R' and R" differ from one another, the reaction between the trihalogenotriazine and the different esters is carried out in stages, if appropriate with isolation, and with purification, if necessary, of the intermediate stage before the subsequent reaction with further ester of p-aminobenzoic acid; however, these synthesis methods and reactions of trihalogenotriazines for the substitution of three halogen atoms by identical or different amine radicals are well known and widely described in the technical literature, especially in the literature dealing with certain types of dyestuffs and optical brighteners.

Some of the esters of the formula (V) are known, and others which are novel are prepared by known methods.

The compounds according to the present invention possess, in addition to very high absorption in the UVB zone, other characteristics which are regarded as necessary for application in practice, for example light stability, heat stability, non-toxicity and so on. In fact, an optimum UVB absorber should have the following properties:

1) High specific extinction E' at 290–320 nm, which means low dosages in use and therefore cost-effectiveness and minimum toxicological risk.
2) Light stability.
3) Heat stability.
4) Oxidation stability.
5) Stability at varying pH.
6) Good solubility, emulsifiability or dispersibility in base substances commonly used as substrates for dermatological formulations.
7) Negligible toxicity.
8) No significant characteristic colour or odour.
9) Relatively high molecular weight, which means a lower probability of absorption by the skin and therefore greater safety from the toxicological viewpoint.
10) Compatibility with the various substances generally used in dermatological formulations.

According to one of the preferred embodiments of the invention, the compositions containing the compounds of the formula (I) are used for protecting the skin from the damaging effects of solar radiations.

The compounds according to the present invention can be added, of course also in combination with other stabilisers, to cosmetic formulations and also to synthetic polymers generally in quantities of between 0.05 and 10%, preferably from 0.1 to 5% by weight of the polymer or cosmetic preparation.

The cosmetic preparations can be of various types and can be used for various purposes. Generally they take the form of ointments, creams, lotions and emulsions.

The compounds of the formula I are added either for protecting the preparations themselves, for example to avoid undesired discolourations, or for protecting the epidermis treated with the cosmetic preparation against the damaging action of UVB radiation, which causes erythema and accelerates ageing of the skin, so that it becomes prematurely dry, wrinkled or scaly.

The examples which follow illustrate the present invention.

EXAMPLE 1

4.6 g of cyanuric chloride and 17.5 g of cyclohexyl p-aminobenzoate are added to 150 ml of xylene. The reaction mixture is stirred under reflux for 6 hours. 100 ml of octane are added, and the mixture is cooled to 0°–5° C. The white crystallised product is filtered off, washed and dried in vacuo.

This gives 16 g of 2,4,6-tris-[p-(cyclohexyloxycarbonyl)-anilino]-s-triazine, melting point: 171°–173° C.

UV (methanol): E'—1691 at 312 nm

EXAMPLES 2–7

The compounds listed in Table 1 are prepared according to the procedure described in Example 1.

TABLE 1

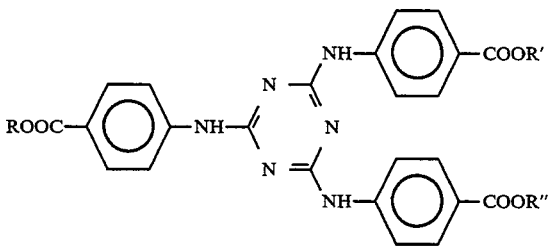

| Example | R = R' = R" | Melting point | E' | nm |
|---|---|---|---|---|
| 2 | 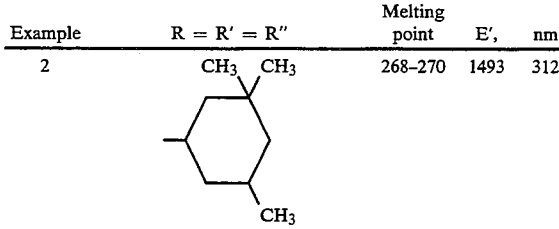 | 268–270 | 1493 | 312 |
| 3 | 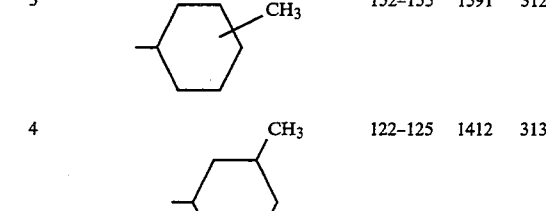 | 152–155 | 1591 | 312 |
| 4 | 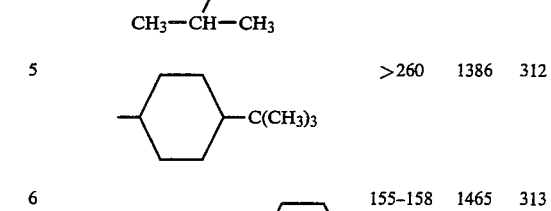 | 122–125 | 1412 | 313 |
| 5 | —⟨cyclohexyl⟩—C(CH₃)₃ | >260 | 1386 | 312 |
| 6 | —CH₂—CH₂—O—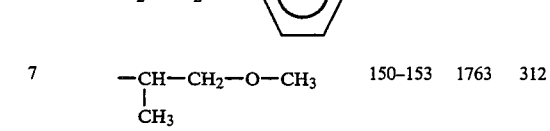 | 155–158 | 1465 | 313 |
| 7 | —CH(CH₃)—CH₂—O—CH₃ | 150–153 | 1763 | 312 |

EXAMPLE 8

6.7 g of sodium bicarbonate are added to a solution of 13.8 g of cyanuric chloride in 150 ml of acetone, cooled to 0° C. A solution of 27.7 g of di-[2-(4-tert-octylphenoxy)-ethyl] 4-aminobenzoate in 100 ml of acetone is slowly added to the mixture obtained, maintaining the temperature at 0°–2° C.

The mixture is stirred for 30 minutes at 0° C., and 50 ml of water are then slowly added. This gives a very dense suspension which is stirred for a further 30 minutes at 0° C. and then filtered, and the filtercake is washed many times with water and then with acetone and dried at 40 ° C. in vacuo. This gives 36 g of 2-[p-[2-(4-tert-octylphenoxy)-ethoxycarbonyl]-anilino]-4,6-dichloro-s-triazine. Melting point: 249°–251° C.

12.8 g of methyl p-aminobenzoate are added to 0.7 g of this intermediate in 200 ml of xylene, and the mixture is stirred for 5 hours under reflux. This xylene is then distilled off, and the residue is crystallised from isopropanol. This gives 19 g of 2-[p-[2-(4-tert-octylphenoxy)-ethoxycarbonyl]anilino]-4,6-bis-[p-(methoxycarbonyl)-anilino]-s-triazine.

Melting point: 157°–160° C.

UV (methanol): $E'=1636$ at 312.6 nm.

EXAMPLES 9–17

Using a similar procedure as described in Example 8, the compounds of Table 2 are prepared.

TABLE 2

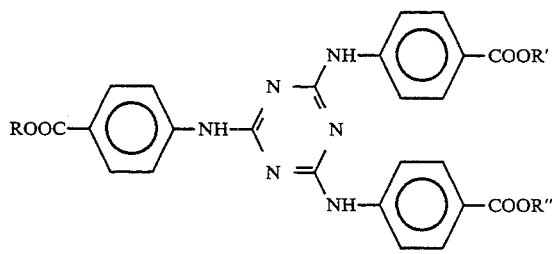

| Example | R | R' = R'' | Melting point | E', | nm |
|---|---|---|---|---|---|
| 9 | ![4-isopropylcyclohexylmethyl] | CH₃ | 217–220 | 1954 | 312 |
| 10 | —CH₂—CH₂—O—[2,4-di-tert-butylphenyl] | CH₃ | 127–130 | 1675 | 313 |
| 11 | —CH₂—CH₂—O—[4-tert-butylphenyl] | CH₃ | 193–195 | 1761 | 313 |
| 12 | —CH₂—CH(C₂H₅)—C₄H₉ | [4-methylcyclohexyl] | 85–88 | 1500 | 313 |
| 13 | —CH₂—CH(C₂H₅)—C₄H₉ | [4-methylcyclohexyl] | 144–147 | 1615 | 313 |
| 14 | —CH₃ | [2,2,4-trimethylcyclohexyl] | 181–184 | 1709 | 313 |
| 15 | —CH₃ | [4-methylcyclohexyl] | 153–156 | 1807 | 312 |

TABLE 2-continued

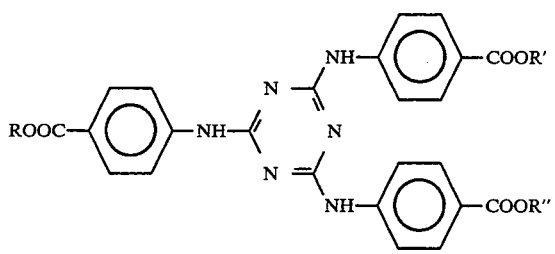

| Example | R | R' = R" | Melting point | E' | nm |
|---|---|---|---|---|---|
| 16 | (4-isopropyl-1-methylcyclohexyl) | C₄H₉ | 161–163 | 1748 | 313 |
| 17 | C₄H₉ | (1-methylcyclohexyl) | 166–168 | 1719 | 313 |

EXAMPLE 18

The SPF of some compounds from the examples described are determined using the method described by B. L. Diffey and J. Robson in J. Soc. Cosmet. Chem. 40, 127–133 (1989).

The results obtained are listed in the table which follows.

TABLE 3

| Example | SPF |
|---|---|
| Compound from Example 3 | 7.6 |
| Compound from Example 4 | 8.2 |
| Compound from Example 10 | 8.5 |
| Compound from Example 13 | 7.7 |
| Compound from Example 14 | 8.5 |
| Compound from Example 15 | 8.4 |
| Compound from Example 16 | 8.3 |
| Compound A | 7.4 |

Compound A is Example 1 described in Patent DE 3,206,398.

EXAMPLE 19

Preparation of a sun cream

A mixture composed of 10 g of cyclodimeticone/dimeticone copolymer (Dow Corning Q2-3225), 10 g of cyclometicone (Dow Corning 344), 0.5 g of polysorbate 20 (Tween 20) and 3 g of the compound of Example 3 is prepared. This mixture is added to a previously prepared solution composed of 0.2 g of 1,1'-methylene-bis-3-(3'-hydroxymethyl-2,4-dioxo-imidazolidinyl)-urea, 0.05 g of methylparaben (methyl p-hydroxybenzoate) and 73.25 g of water.

I claim:

1. An ultraviolet or sunscreening cosmetic composition comprising an effective sunscreening amount of a compound of the formula (I):

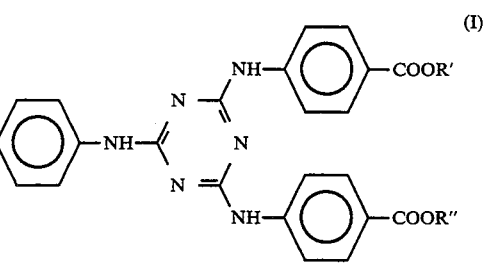

in which

R is C₅–C₁₂cycloalkyl which may be mono- or polysubstituted by C₁–C₄alkyl, or a group of the formula (II), (III) or (IV):

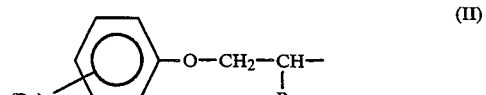

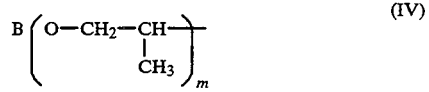

in which R₂ is C₁–C₉alkyl, n can be an integer from 0 to 3,

R₃ is hydrogen or methyl,

A is C₅–C₈cycloalkyl or C₄–C₈alkyl,

B is C₁–C₄alkyl, m can be an integer from 1 to 10, and

R' and R" which are the same or different, can have the same meaning as R or they are selected from the group consisting of hydrogen, an alkali metal, an ammonium group which may be substituted by alkyl or hydroxyalkyl radicals, and $C_1$–$C_{18}$alkyl, and a cosmetic or dematologically acceptable carrier.

2. The compositions of claim 1 wherein the carrier selected from the group consisting of is ointments, creams, lotions and emulsions.

3. The compositions according to claim 1 containing 0.1 to 10% by weight of said compound.

4. The compositions according to claim 1 containing 0.05 to 5% by weight of said compound.

5. The compositions according to claim 1 wherein the compound is contained in the carrier in free-radical deactivating effective amounts of 0.05 to 10%.

6. The compositions of claim 1 wherein the compound is selected from the group consisting of:

2,4,6-tris-[p-(cyclohexyloxycarbonyl)-anilino]-s-triazine;

2,4,6-tris-[p-(3,3,5-trimethylcyclohexyloxycarbonyl)-anilino]-s-triazine;

2,4,6-tris-[p-(methylcyclohexyloxycarbonyl)-anilino]-s-triazine;

2,4,6-tris-[p-(2-isopropyl-5-methylcyclohexyloxycarbonyl)-anilino]s-triazine;

2,4,6-tris-[p-(4-tert-butylcyclhexyloxycarbonyl)-anilino]-s triazine;

2,4,6-tris-[p-(2-phenoxyethoxycarbonyl)-anilino]-s-triazine;

2,4,6-tris-[p-(2-methoxy-1-methylethoxycarbonyl)-anilino]-s-triazine;

2-[p-[2-(4-tert-octylphenoxy)-ethoxycarbonyl]-anilino]-4,6-bis-[p-(methoxycarbonyl)-anilino]-s-triazine;

2-[p-[2-isopropyl-5-methylcyclohexyloxycarbonyl]-anilino]-4,6-bis[p-(methoxycarbonyl)-anilino]-s-triazine;

2-[p-[2-(2,4-ditert-butylphenoxy)-ethoxycarbonyl]-anilino]-4,6-bis-[p-(methoxycarbonyl)-anilino]-s-triazine;

4,6-bis-[p-(2-ethylhexyloxycarbonyl]-anilino]-2-[p-(methylcyclohexyloxycarbonyl)-anilino]-s-triazine;

4,6-bis-[p-(2-ethylhexyloxycarbonyl)-anilino]-2-[p-(cyclohexyloxycarbonyl)-anilino]-s-triazine;

4,6-bis-[p-(methoxycarbonyl)-anilino-2-[p-(3,3,5-trimethylcyclohexyloxycarbonyl)-anilino]-s-trazine;

4,6-bis-[p-(methoxycarbonyl)-anilino]-2-[p-(methycyclohexyloxycarbonyl)-anilino]-s-trazine;

2-[p-(2-isopropyl-5-methylcyclohexyloxycarbonyl)-anilino]-4,6-bis-[p-(butoxycarbonyl)-anilino]-s-triazine; and 4,6-bis-[p-(butoxycarbonyl)-anilino]-2-[p-(methylcyclohexyloxycarbonyl)-anilino]-s-triazine.

* * * * *

UNITED STATES PATENT AND TRADEMARK OFFICE
CERTIFICATE OF CORRECTION

PATENT NO. : 5,393,517
DATED : February 28, 1995
INVENTOR(S) : Giuseppe RASPANTI It is certified that error appears in the above-identified patent and that said Letters Patent is hereby corrected as shown below:

On the title page of the printed patent, in block [75] which identifies the name of the inventor, please change "Raspanti Giuseppe" to --Giuseppe Raspanti--.

Signed and Sealed this

Fourth Day of February, 1997

Attest:

BRUCE LEHMAN

Attesting Officer

Commissioner of Patents and Trademarks